United States Patent [19]
Lee

[11] Patent Number: 6,043,923
[45] Date of Patent: Mar. 28, 2000

[54] MODULATOR AND ELECTRO-OPTIC SENSOR EQUIPPED WITH THE MODULATOR

[75] Inventor: Joong-Kee Lee, Kyongsangbuk-do, Rep. of Korea

[73] Assignee: LG Electronics Inc., Seoul, Rep. of Korea

[21] Appl. No.: 09/207,402

[22] Filed: Dec. 8, 1998

[30] Foreign Application Priority Data

Feb. 16, 1998 [KR] Rep. of Korea .......................... 98-4531

[51] Int. Cl.$^7$ ...................................................... G02F 1/03
[52] U.S. Cl. ........................... 359/245; 359/315; 324/96; 324/753; 324/770; 349/161; 349/122
[58] Field of Search ..................................... 359/245, 257, 359/315; 324/96, 73.1, 753, 754, 770; 349/122, 117, 161, 96

[56] References Cited

U.S. PATENT DOCUMENTS

| | | |
|---|---|---|
| 5,097,201 | 3/1992 | Henley ........................................ 324/96 |
| 5,124,635 | 6/1992 | Henley ........................................ 324/96 |
| 5,170,127 | 12/1992 | Henley ........................................ 324/96 |
| 5,285,150 | 2/1994 | Henley et al. ........................... 324/770 |
| 5,406,213 | 4/1995 | Henley ....................................... 324/753 |
| 5,465,043 | 11/1995 | Sakai ........................................... 324/96 |
| 5,465,052 | 11/1995 | Henley ....................................... 324/770 |
| 5,585,735 | 12/1996 | Takahashi et al. ....................... 324/753 |
| 5,838,415 | 11/1998 | Hayashi et al. .......................... 349/161 |

*Primary Examiner*—Loha Ben

[57] ABSTRACT

A modulator and an electro-optic sensor having the modulator for effectively detecting defects in an LCD panel. The electro-optic sensor includes a modulator including a body, a light reflecting member formed on a portion of the body, and a blower formed on another portion of the body; a light source for generating light to the modulator; and a processing unit for processing a light from the modulator.

20 Claims, 4 Drawing Sheets

MODULATOR AND ELECTRO-OPTIC SENSOR EQUIPPED WITH THE MODULATOR

BACKGROUND OF THE INVENTION

1. Field of the Invention

The present invention relates to a modulator and an electro-optic sensor equipped with a modulator, and more particularly to a modulator and an electro-optic sensor equipped with a modulator for detecting defects in liquid crystal display (LCD) panels and related semiconductor devices.

2. Discussion of the Related Art

An LCD panel contains numerous thin film transistors (TFTs) arranged in an array and pixel electrodes formed on a glass substrate. After the LCD panel is manufactured, a defect level in the LCD panel is diagnosed by an electro-optic sensor using a non-direct contact sensing method.

FIG. 1 is a broad view illustrating a conventional electro-optic sensor. As shown therein, the conventional electro-optic sensor 100 comprises a light source 14 for generating light, a modulator 10 for modulating the light from the light source 14 towards its mirror coating 10-3 and transmitting the light reflected from the mirror coating 10-3 at a certain ratio determined by the strength of its electric field, a beam splitter 12, a lens 16 for focusing the light emitted from the modulator 10, a CCD camera 17 for converting the focused light into an analog video signal, and an image processor 18 for converting the analog video signal into a digital video signal. The digital video signal is displayed on a monitor 20 for analysis.

FIG. 2 is a view illustrating a conventional modulator 10 of the electro-optic sensor 100. The modulator 10 includes a modulator body 10-2, a mirror coating 10-3 and a support frame 10-1. The modulator body 10-2 having a hexagonal shape is supported by the support frame 10-1. The mirror coating 10-3 formed of a thin metal foil is formed on the lower portion of the modulator body 10-2. The modulator body 10-2 includes an electrode commonly connecting with an external voltage source which supplies a reference voltage, and an electro-optic portion formed in the modulator body 10-2 for dispersing the incident light through the modulator body 102 and transmitting the reflected light towards the beam splitter 12 at a certain ratio determined by the strength of electric field in the modulator body 10-2.

The incident light from the light source 14 traverses the modulator body 10-2 and is reflected by the mirror coating 10-3. The reflected light traverses through the modulator body 10-2 and is emitted from the modulator 10 towards the beam splitter 12. During this process, the incident light traverses the modulator body 10-2 and is dispersed therethrough at a certain ratio determined by the strength of electric field in the modulator body 10-2. Consequently, the light emerging out of the modulator 10 has a level that is varied by the electric field strength of the modulator body 10-2.

An operation of the conventional electro-optic sensor and modulator will be explained below. The conventional electro-optic sensor 100 is positioned at a predetermined distance from the surface of the LCD panel 22. Then, a first voltage is applied to the LCD panel 22 as a detection voltage for detecting defects in the LCD panel 22, and a second voltage is also applied to the modulator 10 as a reference voltage. The detection and reference voltages establish a certain electric field in the area, and the electric field response is used to detect defects in the LCD panel 22 without directly emitting a detection signal at the LCD panel 22.

More specifically, when the detection voltage is applied to the picture elements of the LCD panel 22, the response of each picture element varies depending on the condition of the picture element, i.e., whether it is normal or has detects. As a result, each portion of the modulator 10 that corresponds to these picture elements has a different electric field strength. Under this condition, the light incident to the modulator 10 is output from the modulator 10 at a different level according to a predetermined ratio determined by the electric field strength of the modulator 10.

The light emitted from the modulator 10 is focused by the lens 16 and converted into an analog video signal by the CCD camera 17. The image processor 18 converts the analog video signal to a digital video signal. At this time, the condition of the LCD panel 22 is displayed on the monitor 20 based on the digital video signal and the image processing carried out by a central processing unit CPU (not shown). The monitor 20 helps to diagnose the degree of defectiveness in the LCD panel 22 because it displays normal and defective cells of the LCD panel 22 based on the light emerging from the modulator 10.

The conventional electro-optic sensor 20 carries out its operation using a non-contact sensing method since the electro-optic sensor 20 is positioned at a predetermined distance from the surface of the LCD panel 22. Generally, in conventional non-contact sensing methods, the distance between the mirror coating of the modulator and the surface of an LCD panel is no more than 20 $\mu$m.

When a large foreign material (e.g., size equal to or bigger than 20 $\mu$m) attaches to the surface of the LCD panel, the mirror coating of modulator is easily peeled off or damaged due to the contact with the foreign material. The damage to the mirror coating shortens the lifetime of the modulator of the electro-optic sensor. Further, the damaged mirror coating damages the LCD panel since an internal liquid of the modulator can flow out through the mirror coating and contaminate the LCD panel.

SUMMARY OF THE INVENTION

Accordingly, the present invention is directed to a modulator and an electro-optic sensor equipped with a modulator that substantially obviates one or more of the problems due to limitations and disadvantages of the conventional art.

Additional features and advantages of the invention will be set forth in the description which follows and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purposes of the present invention, as embodied and broadly described, a modulator of the present invention comprises: a body through which a light is transmitted, a light reflecting member formed on a first portion of the body; and a blower formed on a second portion of the body.

In another aspect of the present invention, an electro-optic sensor comprises: a modulator including a body through which a light is transmitted, a light reflecting member formed on a first portion of the body, and a blower formed on a second portion of the body; a light source for generating light to the modulator; and a processing unit for processing a light from the modulator.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings. In the present invention, a modulator of an electro-optic sensor includes a blower for moving a foreign or contaminating material away from a surface of an LCD panel and/or a surface of the modulator.

Figure 1:
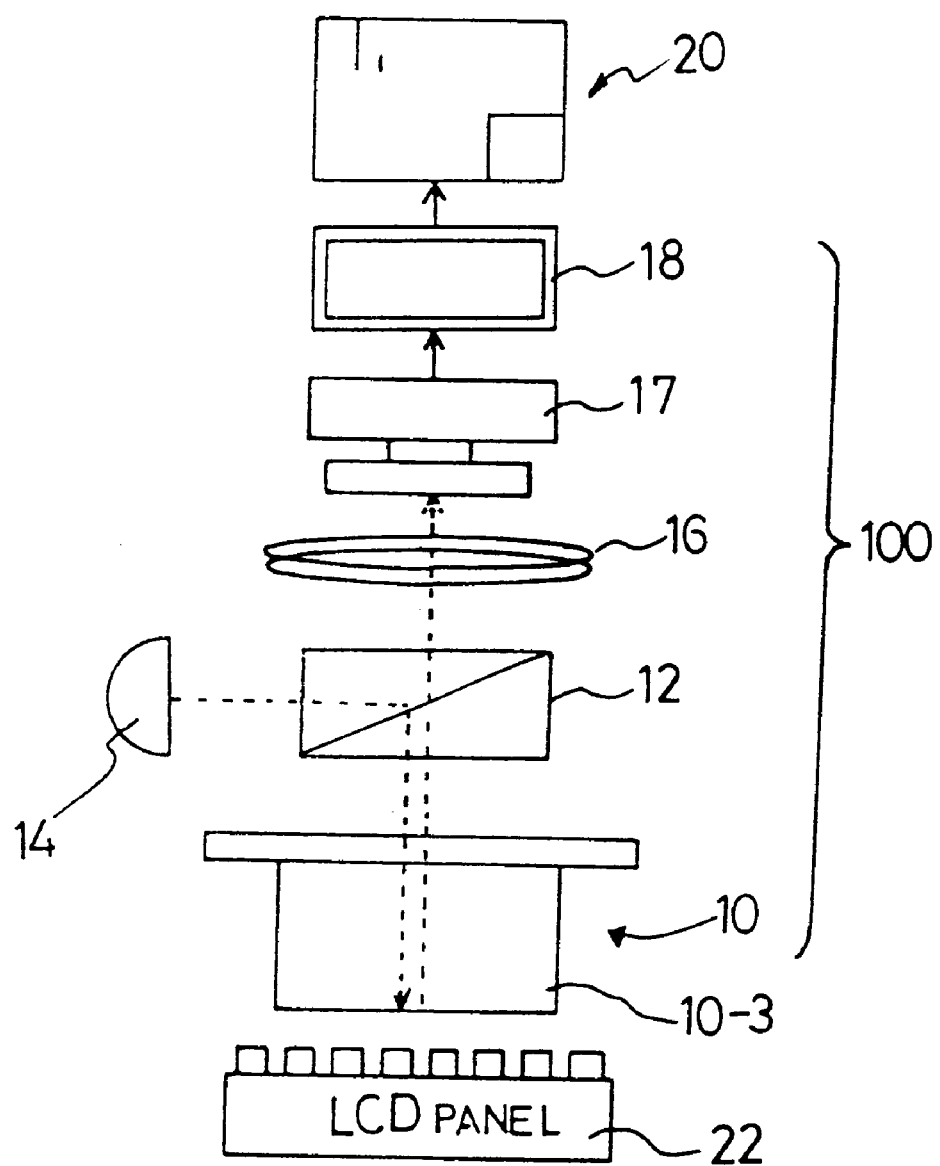
FIG. 1 is a broad view illustrating a conventional electro-optic sensor.
Figure 2:
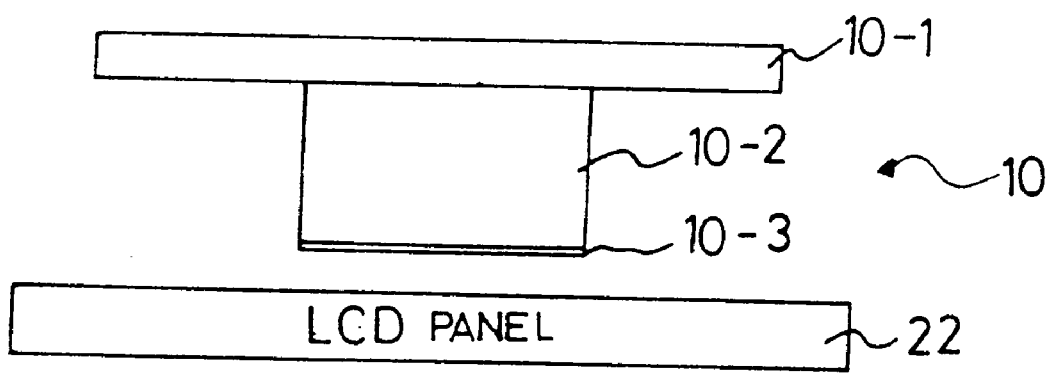
FIG. 2 is a broad view illustrating a modulator of the conventional electro-optic sensor.
Figure 3:
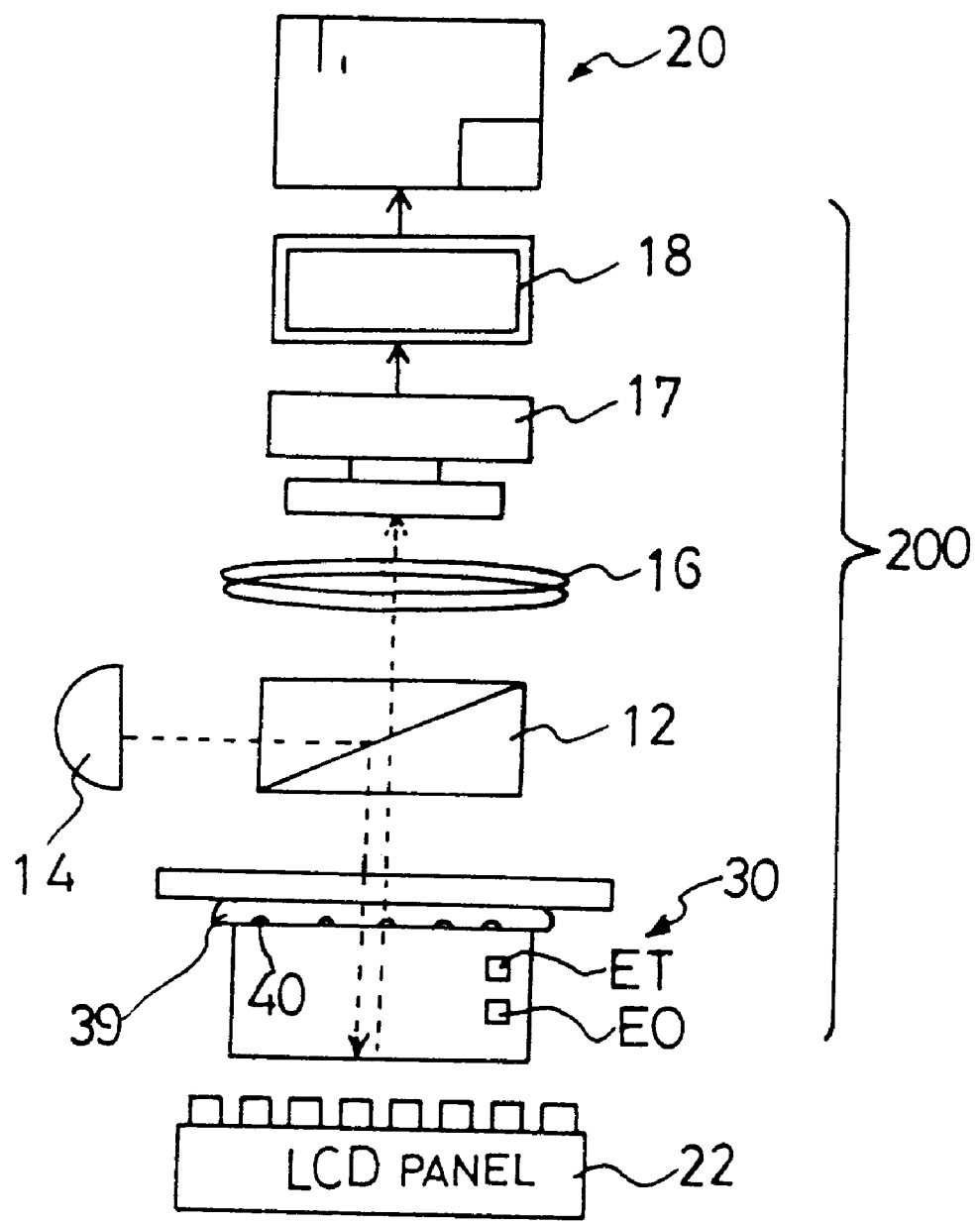
FIG. 3 is a broad view illustrating an electro-optic sensor according to one embodiment of the present invention.

FIG. 3 is a broad view illustrating an electro-optic sensor according to an embodiment of the present invention. As shown therein, the electro-optic sensor 200 of the present invention includes a modulator 30 and elements having the same reference numerals as the conventional electro-optic sensor 100 shown in FIG. 1.

Figure 4:
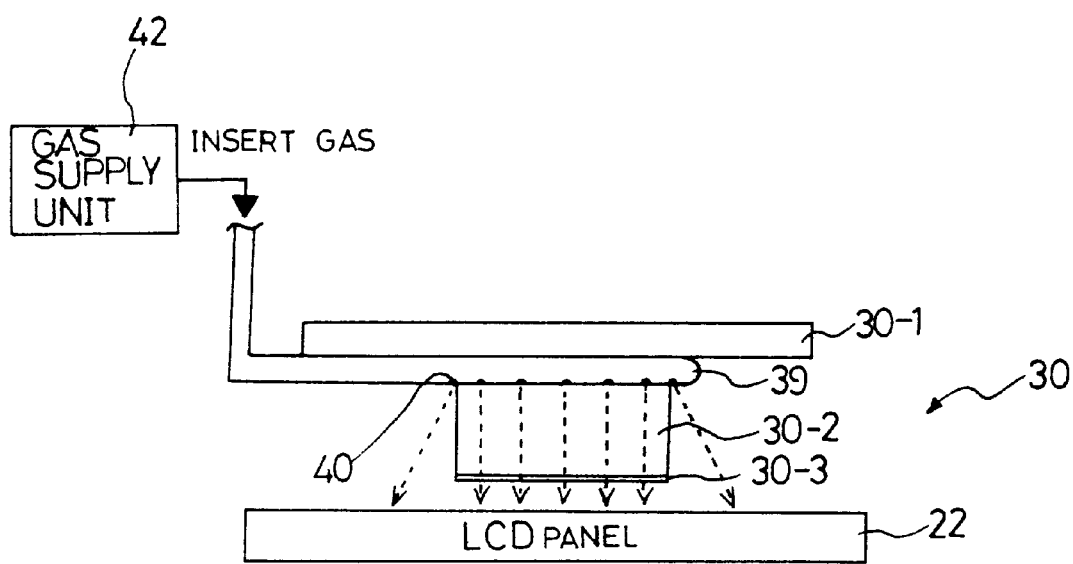
FIG. 4 is a broad view illustrating an example of a modulator of the electro-optic sensor shown in FIG. 3.

The modulator 30 includes a support frame 30-1, a modulator body 30-2, a mirror coating 30-3, and a blower 39 formed at least partially around the modulator body 30-2, as shown in FIG. 4. The modulator body 30-2 of a certain shape, e.g., hexagonal shape, is supported by the support frame 30-1 of a certain shape, e.g., a round plate. Other shapes for the support frame 30-1 and the body 30-2 are contemplated as part of the invention. The mirror coating 30-3 formed of, e.g., a thin metal foil or the like, is formed on a lower portion of the modulator body 30-2.

The modulator body 30-2 includes an electrode portion ET connected with an external voltage source for applying a reference voltage to the body 30-2, and an electro-optic portion EO formed in the modulator body 30-2 for dispersing and transmitting the incident light through the modulator body 30-2 at a certain ratio determined by the electric field strength in the modulator body 30-2.

The blower 39 of the modulator 10 is connected to a gas supply unit 42. The blower 39 has a certain shape, such as, a rectangular tube shape, and surrounds at least a portion of the modulator 30. Other shapes, configurations, and structures for the blower 39 are contemplated as part of the invention. The blower 39 has a plurality of ejection holes 40. The supply unit 42 supplies a gas having a certain pressure through a portion of the blower 39. The gas flows through an interior of the blower 39 and is ejected to the outside through the ejection holes 40. At this time, the ejected gas cleans a surface of the LCD panel 22 by blowing away any contaminating materials or the like from an area around the modulator 30 and/or the LCD panel 22. In this example, the gas is dry and stable so that it does not alter or damage the surfaces of the LCD panel 22 and the modulator 30. Further, the blower 39 can be permanently attached to the modulator 30, or can be detachable and attachable to a portion of the modulator 30 as part of the modulator 30.

In this example, the blower 39 corresponds to the shape of the modulator 30, but the shape of the blower 39 can be triangular, pentagonal, any other polygonal, circular, etc. Furthermore, the blower 30 can be made from various materials, such as, SUS, Teflon, polyurethane, or the like.

An operation of the electro-optic sensor 200 having the modulator 30 according to the present invention will be explained referring to FIGS. 3 and 4.

The modulator 30 is positioned at a predetermined distance from the top surface of the LCD panel 22 (e.g., no more than 20 $\mu$m between the mirror coating 30-2 and the surface of the LCD panel 22). The mirror coating 30-3 can be safely positioned close to the LCD panel 22 without being damaged. At this time, a gas, such as, nitrogen gas, is input into the blower 39 by the gas supply unit 42 in a continuous stream, a pulse jet, etc. The inputted gas flows through the interior of the blower 39 and is ejected to the outer space of the blower 39 through the ejection holes 40. The ejected gas dry-cleans the surface of the LCD panel 22 by blowing away any dust or contaminating materials formed on an area around the modulator 30 and/or a surface of the LCD panel 22.

The ejection holes 40 of the blower 39 can be manipulated to direct the gas at different portions of the modulator 30 and/or the LCD panel 22. For example, the position angle of the ejection holes 40 can be changed manually or through a control unit so that the gas can be directed to most effectively clean the surfaces of the LCD panel 22 and the modulator 30. If the ejection holes 40 are positioned at an angle of about 30 to 60 degrees from the plane perpendicular to the mirror coating 30-3, contaminating materials can be blown away effectively. If the gas were to be inputted into the blower 39 by a pulse jet, it is advantageous to use a high pulse value.

Once the blower 39 has been operated, a first voltage is applied to the LCD panel 22 to establish a detection voltage for detecting defects in the LCD panel 22, and a second voltage is also applied to the modulator 30 to establish a reference voltage. The detection and reference voltages establish a certain electric field in the area, and the electric field response is used to detect defects in the LCD panel 22 without directly emitting a detection signal at the LCD panel 22.

When the detection voltage is applied to the picture elements of the LCD panel 22, the response of each picture element varies depending on the condition of the picture element, i.e., whether it is normal or has defects. As a result, each portion of the modulator 30 that corresponds to these picture elements has a different electric field strength. Under this condition, the light incident to the modulator 30 is output from the modulator 30 at a different level according to a predetermined ratio determined by the electric field strength of the modulator 30.

The light emitted from the modulator 30 is focused by the lens 16 and converted into an analog video signal by the CCD camera 17. The image processor 18 converts the analog video signal to a digital video signal. At this time, the condition of the LCD panel 22 is displayed on the monitor 20 based on the digital video signal and the image processing carried out by a central processing unit CPU (not shown). The monitor 20 helps to diagnose the degree of defectiveness in the LCD panel 22 because it displays normal and defective cells of the LCD panel 22 based on the light emerging from the modulator 30.

In one embodiment of the present invention, the blower is separately prepared to be installed to the modulator. However, in another embodiment, the modulator support frame can function as the blower. This may be achieved by providing a support frame having an interior space which is connected to a gas supply unit and ejection holes formed at predetermined locations on the support frame. That is, the support frame itself can be used as a gas tunnel. This is advantageous because there is no limitation on the space provided between the LCD panel and the support frame, and a separate blower is not needed.

The present invention prevents damage to a modulator due to contacts between the mirror coating of the modulator and any foreign materials when the modulator is located close to the LCD panel for detecting defects in the LCD panel. Also, the present invention prevents contamination of the LCD panel and other related accidents caused by an internal liquid leakage from the modulator due to the damage to the mirror coating. Accordingly, the lifetime of the modulator can be prolonged.

It will be apparent to those skilled in the art that various modifications and variations can be made in a modulator and an electro optic sensor equipped with a modulator of the present invention without departing from the spirit or scope of the invention. Thus, it is intended that the present invention covers the modifications and variations of this invention provided they come within the scope of the appended claims and their equivalents.

What is claimed is:

1. A modulator comprising:
   a body through which a light is transmitted;
   a light reflecting member formed on a first portion of the body; and
   a blower formed on a second portion of the body.

2. The modulator according to claim 1, further comprising:
   a support frame for supporting the body.

3. The modulator according to claim 1, wherein the blower surrounds at least partially the body.

4. The modulator according to claim 1, wherein the body includes a support frame and the blower is integrated into the support frame.

5. The modulator according to claim 4, wherein the support frame includes a plurality of ejection holes.

6. The modulator according to claim 1, wherein the blower includes a plurality of ejection holes.

7. The modulator according to claims 6, wherein the plurality of ejection holes are positioned at an approximately 30 to 60 degree angle from a plane perpendicular to the light reflecting member.

8. The modulator according to claim 1, wherein the blower is selectively attachable and detachable to and from the body.

9. The modulator according to claim 1, wherein the body includes:
   an electrode portion connected to a first voltage source; and
   an electro-optic portion connected to a second voltage source.

10. An electro-optic sensor comprising:
    a modulator including a body, a light reflecting member formed on a portion of the body, and a blower formed on another portion of the body;
    a light source for generating light to the modulator; and
    a processing unit for processing a light from the modulator.

11. The electro-optic sensor according to claim 10, wherein the modulator further includes a support frame for supporting the body of the modulator.

12. The electro-optic sensor according to claim 10, wherein the body includes a support frame, and the blower is integrated into the support frame.

13. The electro-optic sensor according to claim 12, wherein the support frame includes a plurality of ejection holes.

14. The electro-optic sensor according to claim 10, wherein the blower has a tube shape.

15. The electro-optic sensor according to claim 10, wherein a gas is supplied to a first portion of the blower and output through another portion of the blower.

16. The electro-optic sensor according to claim 10, wherein the body includes:
    an electrode portion connected with a first voltage source; and
    an electro-optic portion connected with a second voltage source.

17. The electro-optic sensor according to claim 10, wherein the blower has a plurality of ejection holes.

18. The electro-optic sensor according to claims 17, wherein the plurality of ejection holes are positioned at an approximately 30 to 60 degree angle from a plane perpendicular to the light reflecting member.

19. The electro-optic sensor according to claim 10, wherein the blower is selectively attachable and detachable to and from the body.

20. The electro-optic sensor according to claim 10, wherein the processing unit includes a CCD camera.

* * * * *